US00PP33882P2

(12) United States Plant Patent
Van Swieten

(10) Patent No.: US PP33,882 P2
(45) Date of Patent: Jan. 18, 2022

(54) ***PHALAENOPSIS* ORCHID PLANT NAMED 'PHA1906615'**

(50) Latin Name: ***Phalaenopsis* hybrid**
Varietal Denomination: PHA1906615

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,680

(22) Filed: Sep. 22, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHA1906615', particularly characterized by having light greenish-yellow, dotted flowers with yellow, shaded, and white lips, flowers that are concave in lateral view, yellowish-green flower buds, and is propagated by meristem tissue culture, is disclosed.

3 Drawing Sheets

Genus and species: *Phalaenopsis* hybrid.
Variety denomination: 'PHA1906615'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA1906615'.

The new *Phalaenopsis* plant is a product of a planned breeding program conducted by the inventor in Bleiswijk, the Netherlands. The objective of this breeding program was to create a new *Phalaenopsis* plant with light greenish-yellow, dotted flowers with yellow, shaded, and white lips, suitable for potted plant production.

The new *Phalaenopsis* plant 'PHA1906615' is a result of cross-pollination made by the inventor in February 2013 in Bleiswijk, the Netherlands, of the proprietary female, or seed parent, *Phalaenopsis* hybrid '22286-02' (unpatented) with the proprietary male, or pollen parent, *Phalaenopsis* hybrid '01-1956' (unpatented).

The new *Phalaenopsis* was selected by the inventor as a single plant within the progeny of the stated cross-pollination in a controlled greenhouse in Bleiswijk, the Netherlands, in January 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 22, 2020 (Application no. 2020/2283), by Applicant who obtained the subject matter disclosed directly from the inventor. 'PHA1906615' has not been made publicly available or sold anywhere in the world prior to the effective filing date of this application with the exception of sales or disclosures made one year or less before the effective filing date of this claimed invention by Applicant who obtained 'PHA1906615' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA1906615' as a new and distinct variety of *Phalaenopsis* plant:

1) Light greenish-yellow, dotted flowers with yellow, shaded, and white lips;
2) Flower shape in lateral view is concave; and
3) Flower buds are yellowish-green.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in July 2021. Colors in the photographs may differ from the color values cited in the detailed botanical description, which accurately describe the actual colors of the new variety.

DESCRIPTION OF THE NEW VARIETY

Figure 1:
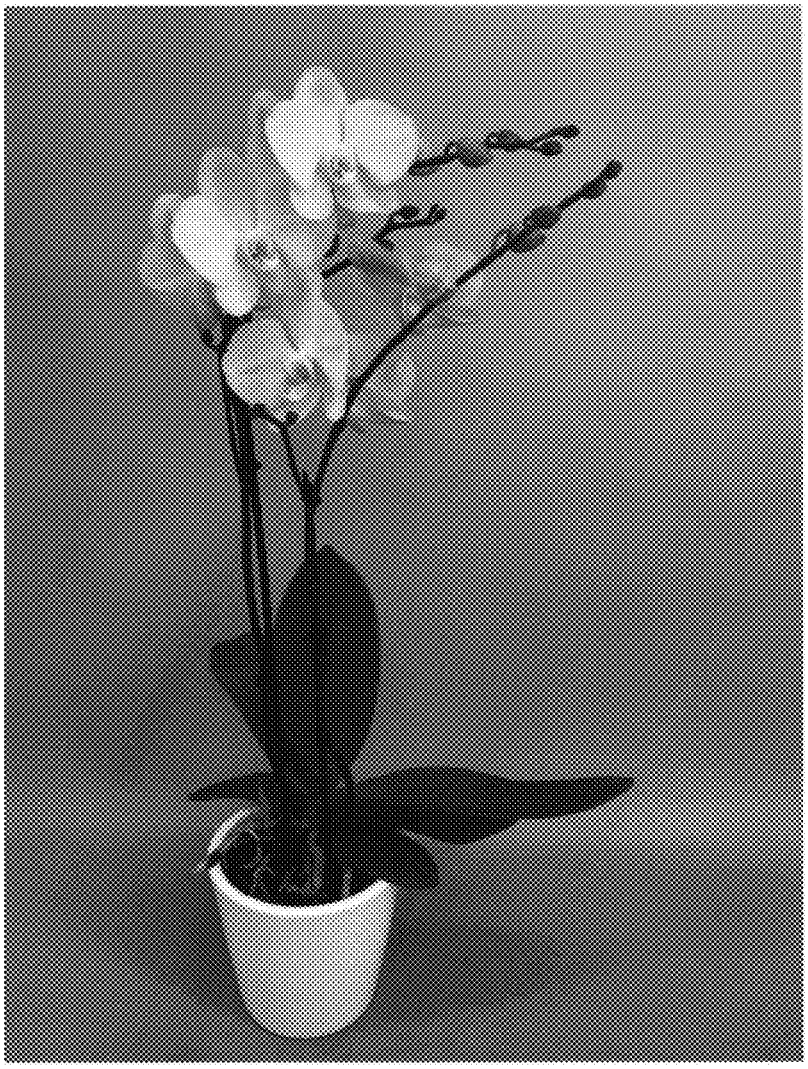
FIG. 1 shows the overall plant habit, including blooms, buds, and foliage of 'PHA1906615'.
Figure 2:
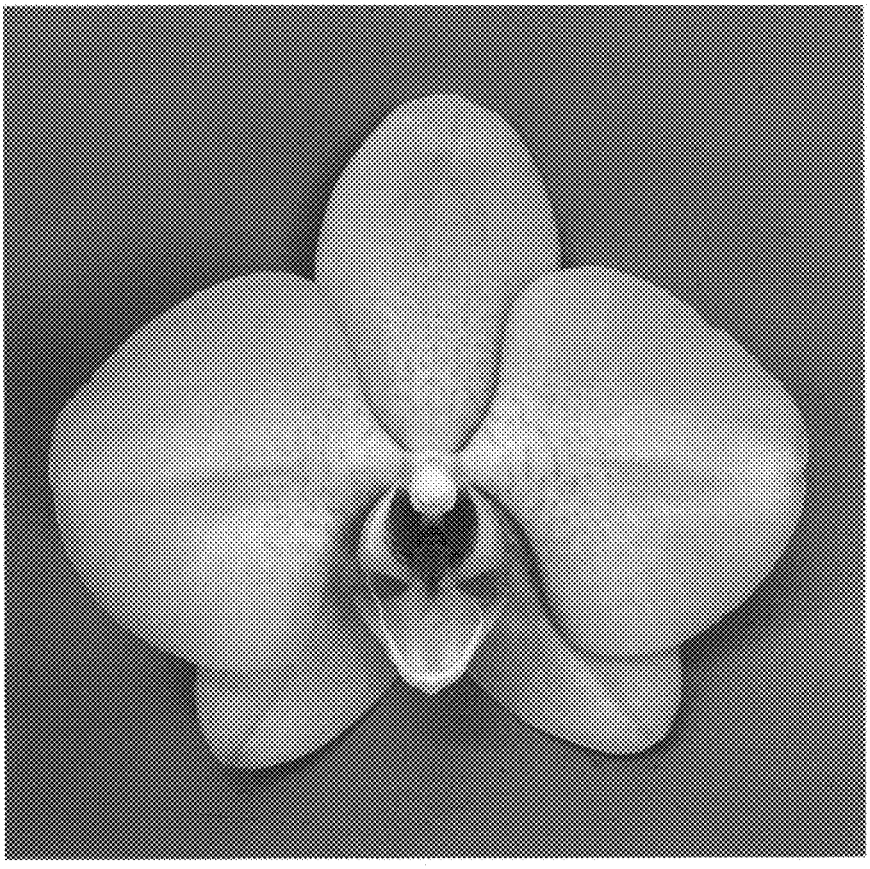
FIG. 2 shows a close-up of a flower of 'PHA1906615'.
Figure 3:
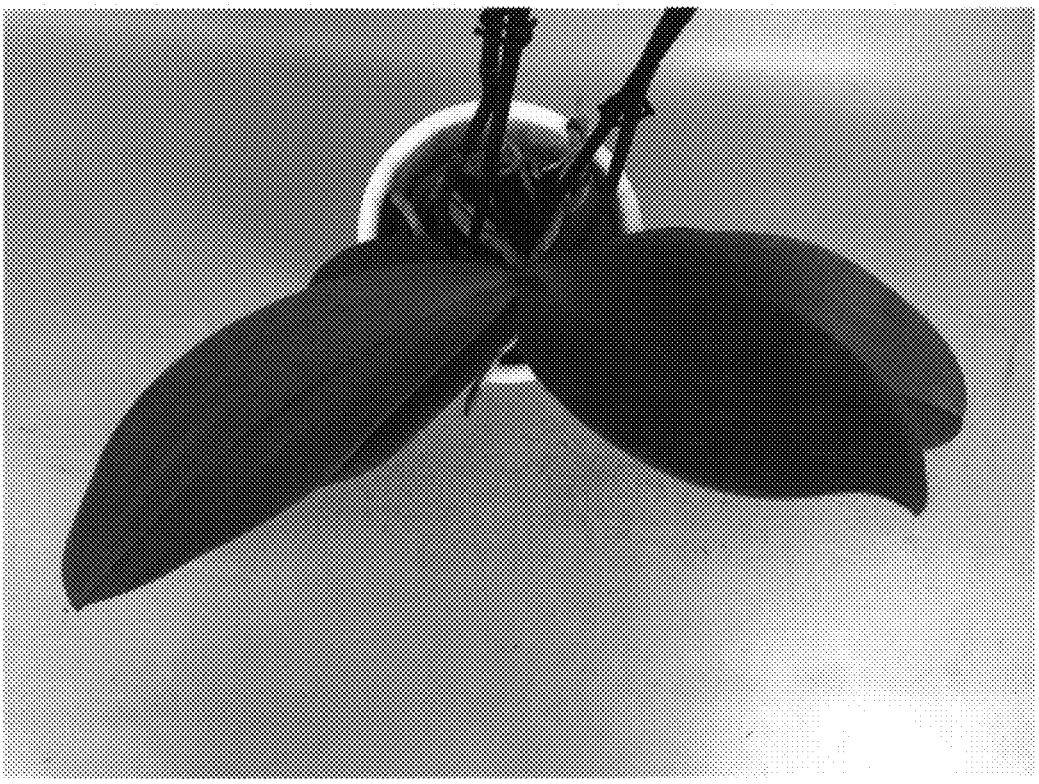
FIG. 3 shows an overhead view of the leaves of 'PHA1906615'.

The following detailed description sets forth the distinctive characteristics of 'PHA1906615'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in July 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA1906615'.

Parentage:

*Female parent*.—*Phalaenopsis* cultivar '22286-02' (unpatented).

*Male parent*.—*Phalaenopsis* cultivar '01-1956' (unpatented).

Propagation:

*Type*.—Meristem tissue culture.

Roots:

*Root description*.—Greyed-green (a color in between RHS 190B and RHS 190C) colored roots with branching lateral roots having yellow-green (RHS N144C) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 55.0 cm to 65.0 cm.

*Width* (*measured from leaf tips*).—About 25.0 cm to 28.0 cm.

*Vigor*.—Strong.

Leaves:

*Mature leaves*.—Quantity per plant: 6 to 8 leaves are produced before flowering. Length (fully expanded): 15.0 cm to 18.0 cm. Width: 7.0 cm to 8.5 cm. Position of the broadest part of the leaf: At the middle. Shape: Oblong. Base shape: Moderately elongated. Apex: Obtuse unequal. Leaf blade angle with the petiole (measured from the horizontal position): Between 20 degrees and 40 degrees. Leaf margin: Entire. Color: Upper surface: RHS 146A. Lower surface: RHS 146B. Texture (both upper and lower surfaces): Smooth. Thickness: 2.1 mm to 2.4 mm. Variegation: Absent. Venation: Pattern: Parallel. Color of the midvein: Upper surface: RHS 146A. Lower surface: RHS 146B.

Peduncle:

*Quantity per plant*.—1 to 2.

*Number of flowers per peduncle*.—10 to 14.

*Length*.—55.0 cm to 65.0 cm.

*Diameter*.—4.0 mm to 5.0 mm.

*Strength*.—Strong.

*Aspect*.—Upright to slightly pendent.

*Texture*.—Smooth.

*Color*.—Mix of dark reddish-brown (RHS 200A) and yellow-green (RHS 146B).

*Internode length*.—4.0 cm to 5.0 cm.

Inflorescence description:

*Appearance*.—Upright to slightly pendent, panicle inflorescence with bilaterally symmetrical flowers that open in succession beginning with the lowermost flower.

*Number of inflorescences*.—1 to 2.

*Inflorescence size*.—Height (from base to tip): 250.0 mm to 280.0 mm.

*Flowering time*.—First flowers can be expected 10 to 11 months after planting in a 12-cm pot.

*Flower*.—Height: 75.0 mm to 80.0 mm. Diameter: 85.0 mm to 90.0 mm. Depth of lip: 21.0 mm to 23.0 mm.

*Flower shape*.—Concave.

*Flower longevity*.—On the plant: 10 to 13 weeks.

*Fragrance*.—Absent.

*Flower bud*.—Average size: Large. Length: 28.0 mm to 30.0 mm. Width: 21.0 mm to 23.0 mm. Shape: Egg shaped. Color: Yellowish-green (RHS N144A).

*Petals*.—Arrangement: Open/free. Shape: Semi-circular. Apex: Slightly emarginated asymmetric. Margin: Moderately undulated. Length (from base to tip): 40.0 mm to 42.0 mm. Width: 46.0 mm to 48.0 mm. Position of the broadest part of the petal: Toward the base. Color (when fully opened): Upper surface: Basic color: Light greenish-yellow (RHS 7D). Over color: Touch of pinkish-white (RHS N155C) with very small light reddish-purple dots (RHS N78D) at the base. Lower surface: Basic color: Light greenish-yellow (RHS 7D). Over color: Touch of light yellow-green (RHS 157C) at the base. Number of spots, dots, and stripes on the petals (upper surface): Few to medium very small dots. Color of spots, dots, and stripes on the petals (upper surface): RHS N78D. Density of netting of the petals (upper surface): None. Color of the netting (upper surface): Not applicable.

*Dorsal sepal*.—Shape: Elliptic. Apex: Obtuse symmetric. Margin: Entire. Length (from base to tip): 43.0 mm to 45.0 mm. Width: 29.0 mm to 31 0 mm. Position of the broadest part of the dorsal sepals: At the middle. Color (when fully opened): Upper surface: Basic color: Light greenish-yellow (RHS 5C). Over color: Touch of pinkish-white (RHS N155C) with very small purplish-pink dots (RHS N78C) at the base. Lower surface: Basic color: Light greenish-yellow (RHS 5C). Over color: Touch of light yellow-green (RHS 157C) at the base; greenish-yellow (RHS 151A). Number of spots, dots, and stripes on the dorsal sepals (upper surface): Few to medium very small dots. Color of spots, dots, and stripes on the dorsal sepals (upper surface): RHS N78C. Density of netting of the dorsal sepals (upper surface): None. Color of the netting: Not applicable.

*Lateral sepals*.—Shape: Ovate. Apex: Obtuse symmetric. Margin: Weakly undulated. Length (from base to tip): 42.0 mm to 44.0 mm. Width: 26.0 mm to 28.0 mm. Position of the broadest part of the lateral sepals: At the base. Color (when fully opened): Upper surface: Basic color: Light greenish-yellow (RHS 5C). Over color: Touch of pinkish-white (RHS N155C) with very small purplish-pink dots (RHS N78C) at the base. Lower surface: Basic color: Light greenish-yellow (RHS 5C). Over color: Greenish-yellow (RHS 151D) at the middle. Number of spots, dots, and stripes on the lateral sepals (upper surface): Few to medium very small dots. Color of spots, dots, and stripes on the lateral sepals (upper surface): RHS N78C. Density of netting of the lateral sepals (upper surface): None. Color of the netting (upper surface): Not applicable.

*Labellum* (*lip*).—Whiskers: Present. Length of whiskers: 16.0 mm to 18.0 mm. Color of whiskers: White (RHS NN155C) with light greenish-yellow tips (RHS 8B). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Widely undulated. Length: 16.0 mm to 18.0 mm. Width: 8.0 mm to 10.0 mm. Color: Upper surface: Light greenish-yellow (RHS 8C) and striped (RHS 187C) at the base; yellow (RHS 13A) on one margin; white (RHS NN155C) toward margin on the other side and the tip. Lower surface: Yellowish-white (RHS 158C); yellow margin (RHS 13A) on one side; white (RHS NN155C) toward margin on the other side and the tip. Number of spots and stripes on the lateral lobe: Medium stripes. Color of spots and stripes on the lateral lobe: RHS 187C. Density of netting of the lateral lobe: None. Color of the netting: Not applicable.

*Apical lobe*.—Shape: Trullate. Margin: Entire. Length: 27.0 mm to 29.0 mm. Width: 20.0 mm to 22.0 mm. Color: Upper surface: Yellow (RHS 12A) with reddish-orange shade (RHS 175D) at the base; white (RHS NN155C) toward whiskers. Lower surface: Yellow (RHS 12A); shaded wings (RHS 176D); white (RHS NN155C) at the middle from base toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Small. Height: 4.0 mm to 5.0 mm. Length: 4.0 mm to 5.0 mm. Width: 3.0 mm to 4.0 mm. Color: Yellow (RHS 14A); dotted (RHS 187C).

Reproductive organs:

*Column*.—Length: 9.0 mm to 11.0 mm. Diameter: 5.0 mm to 6.0 mm. Color: White (RHS NN155C) with a hint of light purple (RHS 76A) at the base.

*Pollinia*.—Quantity: 2. Diameter: 0.8 mm to 1.0 mm. Color: Orange-yellow (RHS 17A).

*Ovary*.—Length: 10.0 mm to 12.0 mm. Diameter: 2.3 mm to 2.5 mm.

*Pedicel*.—Length: 32.0 mm to 34.0 mm. Diameter: 2.6 mm to 2.9 mm. Color: Yellow-green (RHS 145B) at the base and lighter yellow-green (RHS 145C) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA1906615' differs from the female parent plant '22286-02' (unpatented) in that 'PHA1906615' has flowers with a main color of light greenish-yellow, whereas '22286-02' has flowers with a main color of greenish-yellow. Additionally, 'PHA1906615' has larger flowers than '22286-02'.

'PHA1906615' differs from the male parent plant '01-1956' (unpatented) in that 'PHA1906615' has flowers with a main color of light greenish-yellow and a dotted and centered pattern, whereas '01-1956' has flowers with a main color of white and an even pattern. Additionally, 'PHA1906615' has smaller flowers than '01-1956'.

'PHA1906615' is most similar to the commercial *Phalaenopsis* plants named 'PHALGLAZAL' (U.S. Plant Pat. No. 29,909) and 'PHALGOBI' (U.S. Plant Pat. No. 31,804). 'PHA1906615' differs from the commercial variety 'PHALGLAZAL' in that 'PHA1906615' has trullate apical lobes and slightly emarginated petal apexes, whereas 'PHALGLAZAL' has rhombic apical lobes and rounded petal apexes. Additionally, 'PHA1906615' has longer whiskers than 'PHALGLAZAL'.

'PHA1906615' differs from the commercial variety 'PHALGOBI' in that 'PHA1906615' has trullate apical lobes, slightly emarginated petal apexes, and flowers with a dotted and centered pattern, whereas 'PHALGOBI' has triangular apical lobes, obtuse petal apexes, and flowers with an even pattern.

I claim:

1. A new and distinct variety of *Phalaenopsis* plant named 'PHA1906615', substantially as described and illustrated herein.

* * * * *